United States Patent
Yamazaki

(10) Patent No.: US 9,468,410 B2
(45) Date of Patent: Oct. 18, 2016

(54) X-RAY CT APPARATUS AND X-RAY DIAGNOSIS APPARATUS

(71) Applicant: Toshiba Medical Systems Corporation, Otawara-shi (JP)

(72) Inventor: Takayuki Yamazaki, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 141 days.

(21) Appl. No.: 14/506,808

(22) Filed: Oct. 6, 2014

(65) Prior Publication Data

US 2015/0110241 A1  Apr. 23, 2015

(30) Foreign Application Priority Data

Oct. 18, 2013  (JP) .................. 2013-217913

(51) Int. Cl.
*A61B 6/00* (2006.01)
*A61B 6/03* (2006.01)
*H04N 5/32* (2006.01)

(52) U.S. Cl.
CPC ............ *A61B 6/032* (2013.01); *A61B 6/4233* (2013.01); *A61B 6/5205* (2013.01); *A61B 6/585* (2013.01); *H04N 5/32* (2013.01); *A61B 6/56* (2013.01)

(58) Field of Classification Search
CPC .... A61B 6/032; A61B 6/4233; A61B 6/585; A61B 6/5205; A61B 6/56; H04N 5/32
USPC ...................................... 378/4–20
See application file for complete search history.

(56) References Cited

U.S. PATENT DOCUMENTS 7,050,528 B2 *  5/2006  Chen ............... G06T 11/005
378/4

FOREIGN PATENT DOCUMENTS

| JP | 2000-51196 | 2/2000 |
|---|---|---|
| JP | 2005-349187 | 12/2005 |
| JP | 2007-175154 | 7/2007 |
| JP | 2012-157742 | 8/2012 |
| JP | 2012-200555 | 10/2012 |
| JP | 2013-173033 | 9/2013 |

* cited by examiner

*Primary Examiner* — Courtney Thomas
(74) *Attorney, Agent, or Firm* — Oblon, McClelland, Maier & Neustadt, L.L.P.

(57) ABSTRACT

An X-ray CT apparatus includes: an X-ray detector in which detecting elements that detect X-rays are arranged in a body-axis direction and a rotation direction; an acquiring unit that acquires signals of the X-rays detected by at least one group of detecting elements which includes a predetermined quantity of detecting elements and in which detecting elements are arranged in at least the rotation direction and that, when reading the signals detected by the detecting elements arranged in the rotation direction from the X-ray detector, sequentially reads the signals at times that vary among the detecting elements arranged in the rotation direction; a correction signal acquiring unit that, in accordance with the signal reading times, acquires correction signals used in a correcting process performed when an image is generated; and an image generating unit that generates the image by applying each correction signal to a corresponding one of the signals.

11 Claims, 12 Drawing Sheets

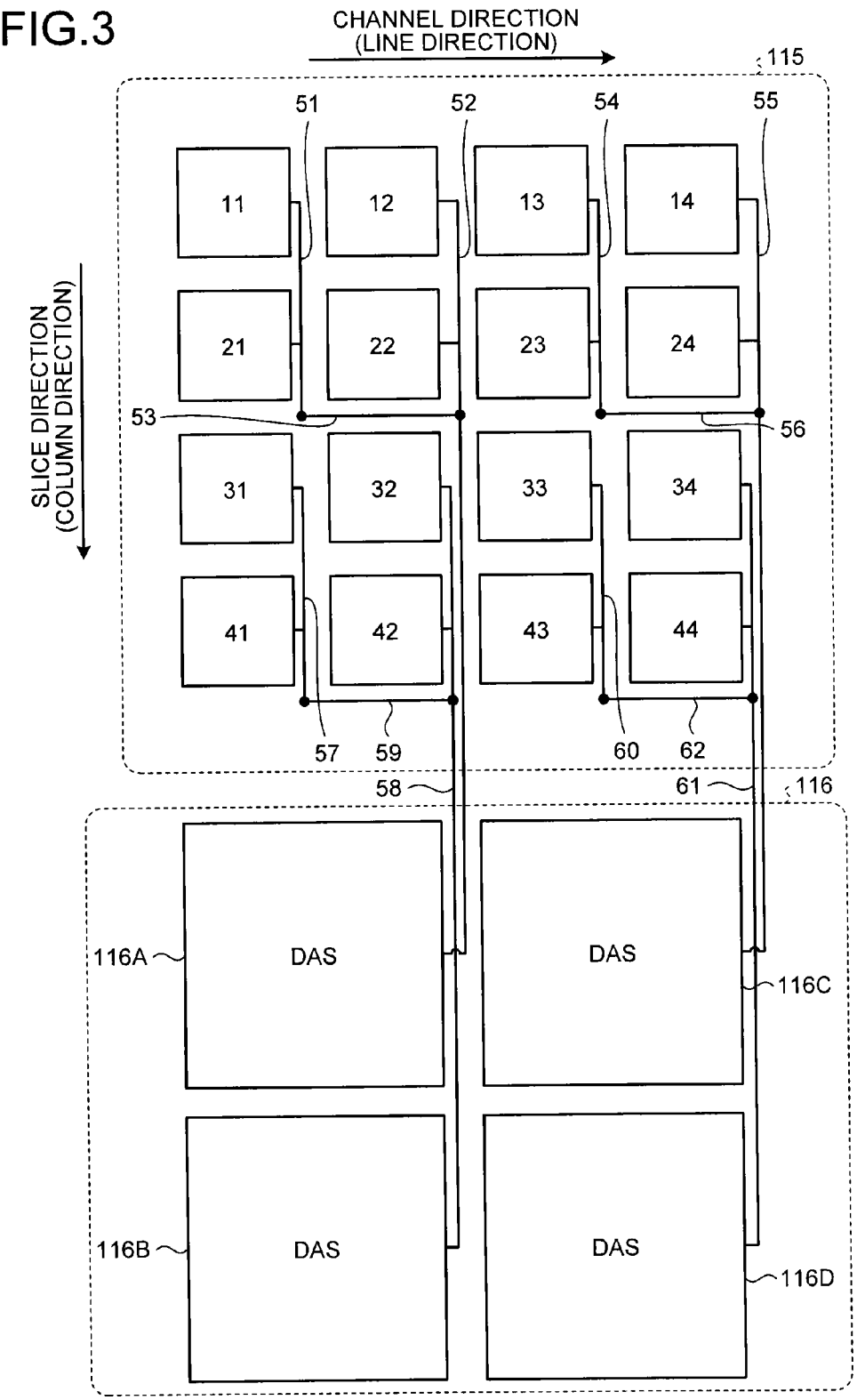

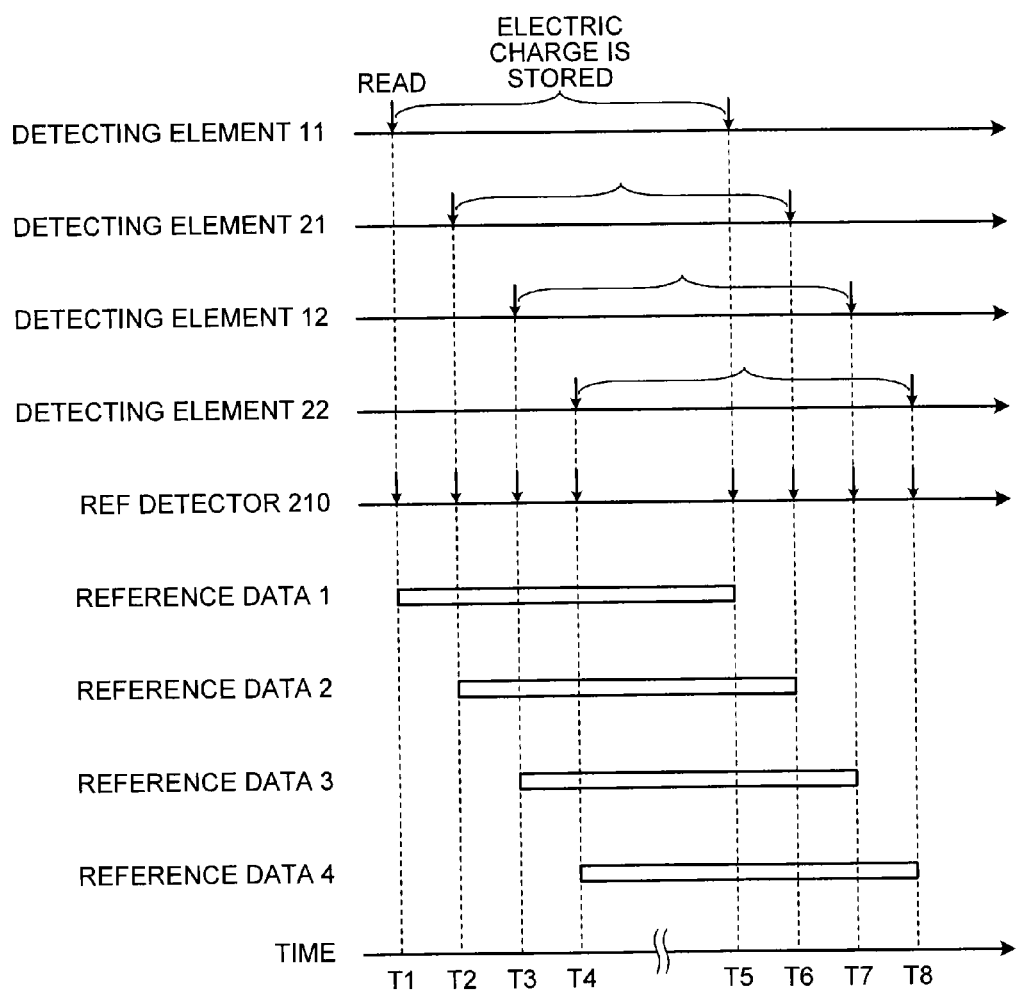

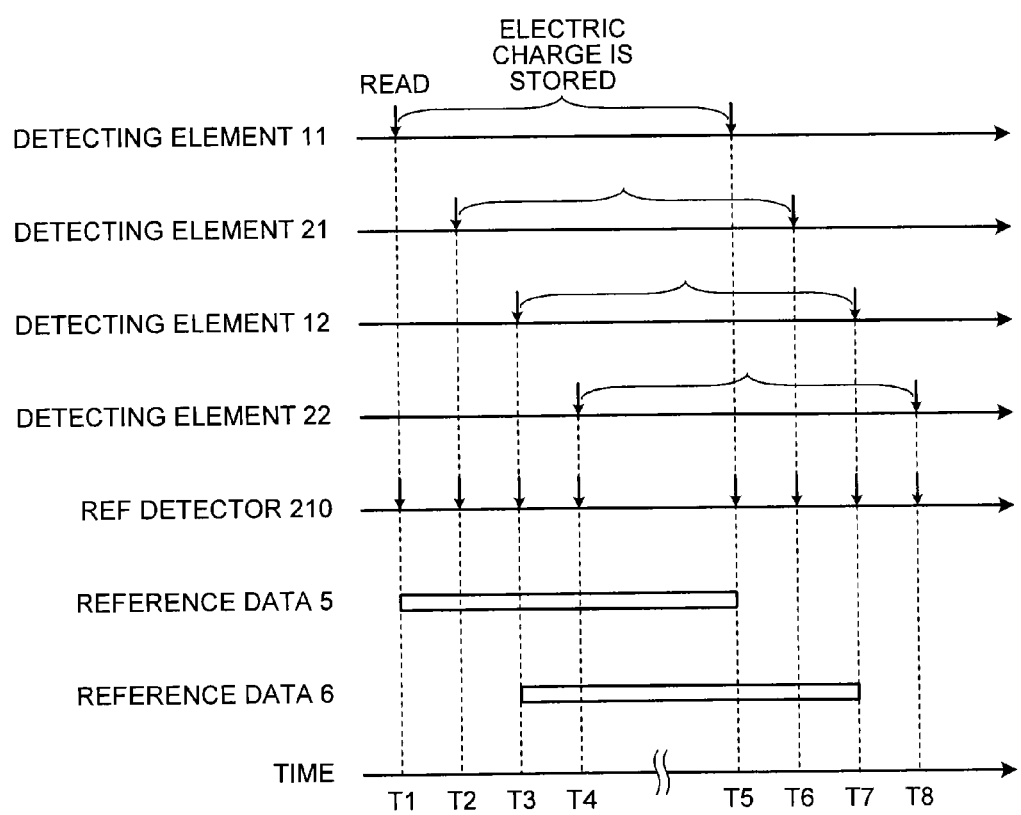

US 9,468,410 B2

X-RAY CT APPARATUS AND X-RAY DIAGNOSIS APPARATUS

CROSS-REFERENCE TO RELATED APPLICATIONS

This application is based upon and claims the benefit of priority from Japanese Patent Application No. 2013-217913, filed on Oct. 18, 2013; the entire contents of which are incorporated herein by reference.

FIELD

Embodiments described herein relate generally to an X-ray CT apparatus and an X-ray diagnosis apparatus.

BACKGROUND

X-ray Computed Tomography (CT) apparatuses are apparatuses configured to image the inside of an examined subject by scanning the subject with the use of X-rays and processing acquired data with a computer.

More specifically, an X-ray CT apparatus is configured to emit X-rays onto a subject multiple times from mutually-different directions and to detect signals of X-rays that have passed through the subject by using an X-ray detector. The X-ray detector is a multi-row detector that includes a plurality of X-ray detecting elements that are arranged in a channel direction (a rotation direction) and a slice direction (a body-axis direction). The X-ray CT apparatus is configured to acquire the detected signals and generates projection data by applying an analog/digital (A/D) conversion thereto and subsequently applying a pre-processing process and the like thereto. After that, the X-ray CT apparatus generates image data by performing a reconstructing process based on the projection data.

Further, the X-ray CT apparatus performs a "signal bundling process" to bundle the signals detected by the plurality of detecting elements arranged in the slice direction, in order to achieve a desired level of spatial resolution or in order to achieve a desired signal-to-noise (S/N) ratio, with respect to the generated image data.

BRIEF DESCRIPTION OF THE DRAWINGS

FIG. 3 is a drawing for explaining a positional relationship between Data Acquisition Systems (DASs) and detecting elements according to the first embodiment;

FIGS. 9A to 9C are drawings for explaining generation of reference data according to the second embodiment.

DETAILED DESCRIPTION

Exemplary embodiments of an X-ray CT apparatus will be explained below, with reference to the accompanying drawings. Possible embodiments are not limited to the exemplary embodiments described below.

First Embodiment

Figure 1:
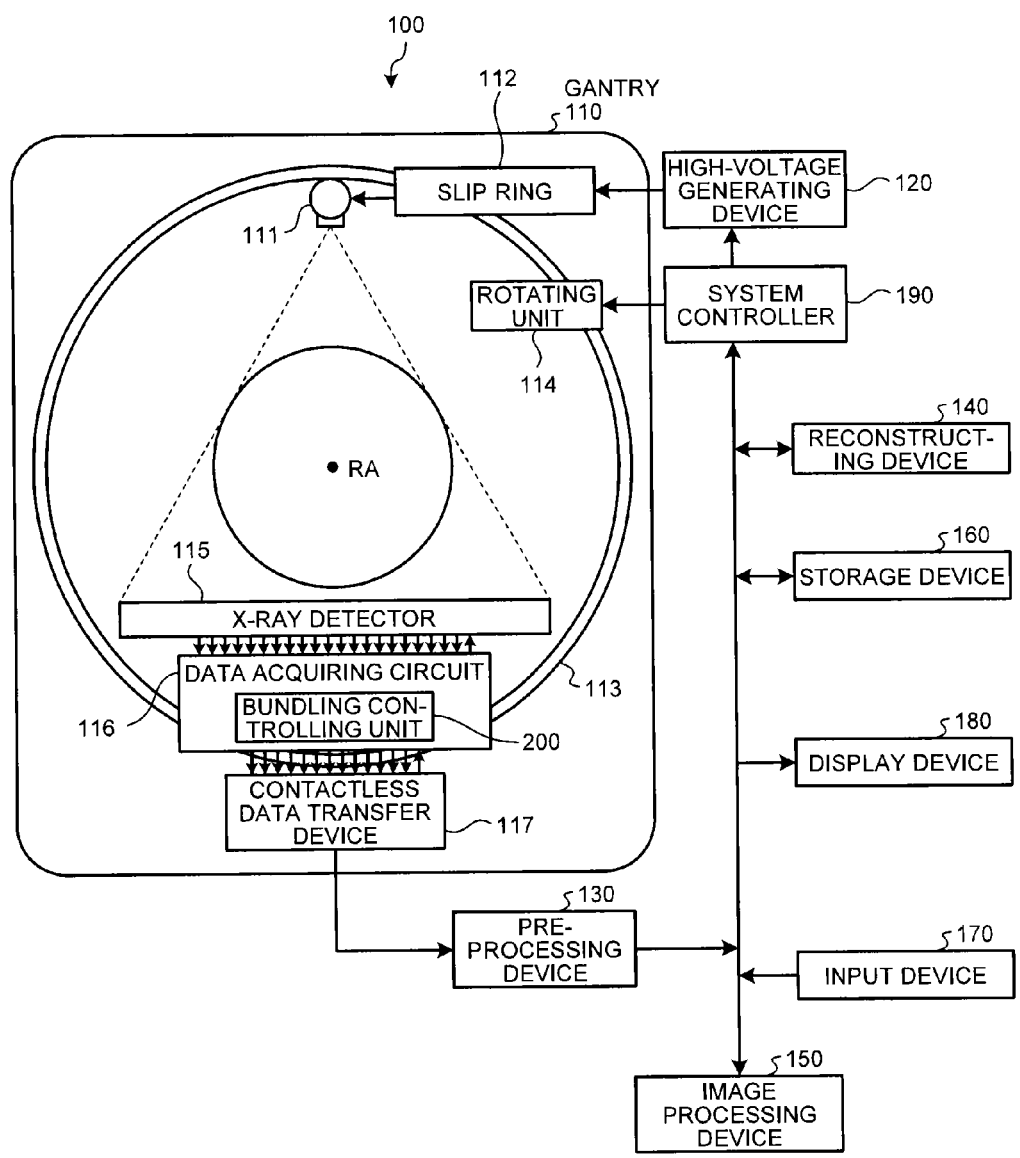
FIG. 1 is a drawing of a configuration of an X-ray CT apparatus according to a first embodiment.

FIG. 1 is a drawing of a configuration of an X-ray CT apparatus 100 according to the first embodiment. As illustrated in FIG. 1, the X-ray CT apparatus 100 includes a gantry 110, a high-voltage generating device 120, a pre-processing device 130, a reconstructing device 140, an image processing device 150, a storage device 160, an input device 170, a display device 180, and a system controller 190.

The gantry 110 is configured to generate raw data by emitting X-rays onto an examined subject and detecting X-rays that have passed through the subject. The gantry 110 includes an X-ray tube 111, a slip ring 112, an X-ray detector 115, a frame 113, a rotating unit 114, a data acquiring circuit 116, and a contactless data transfer device 117.

The X-ray tube 111 is configured to generate the X-rays to be emitted onto the subject, by using an X-ray tube voltage and an X-ray tube current supplied from the high-voltage generating device 120 via the slip ring 112. The X-ray detector 115 is configured to detect the X-rays that were generated from the X-ray tube 111 and have passed through the subject. The X-ray detector 115 will be explained in detail later.

The frame 113 is formed so as to have an annular shape and is configured to be rotatable while a rotation axis RA is used as the center of rotation. The frame 113 supports the X-ray tube 111 and the X-ray detector 115 in such a manner that X-ray tube 111 and the X-ray detector 115 oppose each other while the rotation axis RA is interposed therebetween. The rotating unit 114 is configured to rotate the frame 113 while the rotation axis RA is used as the center of rotation. For example, the rotating unit 114 rotates the frame 113 at a high speed such as 0.4 seconds per rotation. With these arrangements, the rotating unit 114 causes the X-ray tube 111 and the X-ray detector 115 to rotate around the body axis of the subject.

The X-ray detector 115 is a multi-row detector (which may be called a "multi-slice detector" or "multi-detector-row detector") that includes a plurality of X-ray detecting elements (hereinafter, simply "detecting elements") that are arranged in a channel direction (a line direction) and a slice direction (a column direction). The channel direction corresponds to the rotation direction of the frame 113, whereas the slice direction corresponds to the body-axis direction of the subject.

Figure 2A:
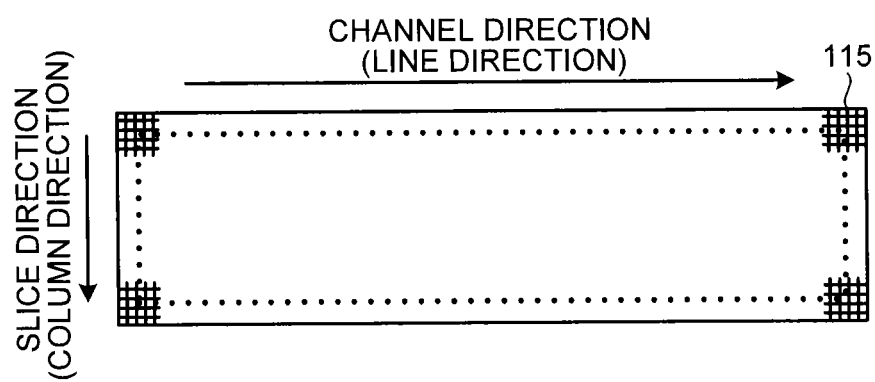
FIGS. 2A and 2B are drawings for explaining an X-ray detector according to the first embodiment.
Figure 2B:
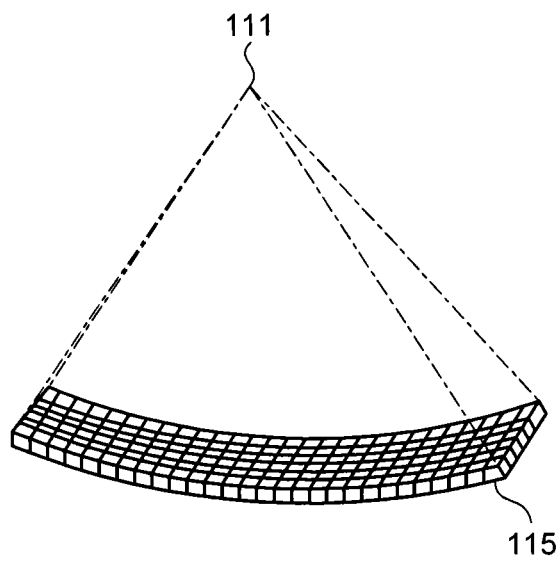

FIGS. 2A and 2B are drawings for explaining the X-ray detector 115 according to the first embodiment. FIG. 2A is a top view illustrating a configuration of the X-ray detector 115. As illustrated in FIG. 2A, for example, the X-ray detector 115 includes the plurality of detecting elements that are arranged in the channel direction (the line direction) and the slice direction (the column direction). FIG. 2B is a perspective view.

For example, each of the detecting elements included in the X-ray detector 115 is configured to detect X-rays that have passed through the subject. After that, each of the detecting elements stores therein an electric charge in accordance with the detected amount of X-rays. The electric charge stored in each of the detecting elements is read, as necessary, by the data acquiring circuit 116 (explained later). In other words, the electric charge stored in each of the detecting elements is sent to the data acquiring circuit 116 as a signal of the X-rays that have passed through the subject (hereinafter, "X-ray transmission signal"). In the first embodiment, an example is explained in which the plurality of X-ray detecting elements each having a width of 0.5 mm are arranged in the channel direction and the slice direction. However, possible embodiments are not limited to this example. For instance, it is acceptable to arrange X-ray detecting elements each having a width of 1 mm.

The data acquiring circuit 116 includes a plurality of Data Acquisition Systems (DASs). The DASs are configured to read (acquire) the signals of the X-rays (the X-ray transmission signals) detected by the X-ray detector 115, to amplify the read signals, and to further convert the amplified signals into data of digital signals (raw data). The contactless data transfer device 117 is configured to transmit the raw data output from the DASs to the pre-processing device 130.

In the present example, each of the DASs according to the first embodiment is in charge of a plurality of detecting elements in the channel direction and the slice direction. In other words, the relationship between the DASs and the detecting elements is not a one-to-one relationship. Each of the DASs processes signals detected by a group of detecting elements. In this situation, the group of detecting elements is, for example, a set of a plurality of detecting elements in which a plurality of detecting elements are arranged in the channel direction and in the slice direction. The DASs correspond to an example of an acquiring unit.

FIG. 3 is a drawing for explaining a positional relationship between the DASs and the detecting elements according to the first embodiment. FIG. 3 illustrates a part of the detecting elements provided in the X-ray detector 115 illustrated in FIG. 2. In the example in FIG. 3, four DASs, namely DASs 116A, 116B, 116C, and 116D, are provided for sixteen detecting elements 11, 12, 13, 14, 21, 22, 23, 24, 31, 32, 33, 34, 41, 42, 43, and 44. With reference to FIG. 3, the example is explained in which four detecting elements in a group of detecting elements is assigned to each of the DASs. However, possible embodiments are not limited to this example. For instance, the quantity of detecting elements included in each group of detecting elements may arbitrarily be changed. Further, another arrangement is also acceptable in which each of the DASs is in charge of processing the signals detected by two or more groups of detecting elements.

In FIG. 3, the DAS 116A is in charge of processing signals detected by the detecting elements 11, 12, 21, and 22. In this situation, the detecting elements 11 and 12 are present in mutually-different positions in the channel direction. Also, the detecting elements 21 and 22 are present in mutually-different positions in the channel direction. Further, the detecting elements 11 and 21 are present in mutually-different positions in the slice direction. Also, the detecting elements 12 and 22 are present in mutually-different positions in the slice direction. Further, a lead wire 51 is configured to connect the detecting elements 11 and 21 together that are provided in the same channel. Further, a lead wire 52 is configured to connect the detecting elements 12 and 22 together that are provided in the same channel. Furthermore, a lead wire 53 is configured to connect the lead wires 51 and 52 together. In addition, the lead wires 51, 52, and 53 are connected to the DAS 116A. In the example illustrated in FIG. 3, the lead wire 52 is connected to the DAS 116A. Provided between the detecting elements 11, 12, 21, 22 and the DAS 116A are switches configured to individually switch the connection and the disconnection between the detecting elements and the DAS. By controlling the switches individually, the electric charges stored in the detecting elements are sequentially read by the DAS 116A. Further, in the present description, for the sake of convenience in the explanation, the example in which the lead wires 51, 52, and 53 are each connected is explained. However, possible embodiments are not limited to this example. For instance, the lead wires 51, 52, and 53 may be configured with a single lead wire.

Further, the DAS 116B is in charge of processing signals detected by the detecting elements 31, 32, 41, and 42. In this situation, the positional relationship among the DAS 116B, the detecting elements 31, 32, 41, and 42, and lead wires 57, 58, and 59 is the same as the positional relationship among the DAS 116A, the detecting elements 11, 12, 21, and 22, and the lead wires 51, 52, and 53.

In addition, the DAS 116C is in charge of processing signals detected by the detecting elements 13, 14, 23, and 24. In this situation, the positional relationship among the DAS 116C, the detecting elements 13, 14, 23, and 24, and lead wires 54, 55, and 56 is the same as the positional relationship among the DAS 116A, the detecting elements 11, 12, 21, and 22, and the lead wires 51, 52, and 53.

Furthermore, the DAS 116D is in charge of processing signals detected by the detecting elements 33, 34, 43, and 44. In this situation, the positional relationship among the DAS 116D, the detecting elements 33, 34, 43, and 44, and lead wires 60, 61, and 62 is the same as the positional relationship among the DAS 116A, the detecting elements 11, 12, 21, and 22, and the lead wires 51, 52, and 53.

As explained above, the DASs 116A to 116D are in charge of processing the signals detected by the detecting elements 11 to 44. The DASs 116A to 116D are capable of performing processes in parallel to one another.

Further, the data acquiring circuit 116 includes a bundling controlling unit 200. Processes performed by the bundling controlling unit 200 will be explained later.

Returning to the description of FIG. 1, the high-voltage generating device 120 is a device configured to cause the X-rays to be generated by supplying the X-ray tube voltage and the X-ray tube current to the X-ray tube 111 included in the gantry 110. The pre-processing device 130 is configured to generate projection data from which an image is reconstructed, by performing a correcting process such as a sensitivity correcting process on the raw data transmitted from the contactless data transfer device 117.

The reconstructing device 140 is configured to reconstruct image data of the subject, by performing a predetermined reconstructing process on the projection data generated by the pre-processing device 130. The image processing device 150 is configured to generate a three-dimensional image, a curve Multi Planar Reconstruction (MPR) image, a cross-cut image, or the like, by using the image data reconstructed by the reconstructing device 140.

The storage device 160 is configured to store therein the projection data generated by the pre-processing device 130, the image data reconstructed by the reconstructing device 140, various types of images generated by the image processing device 150, and the like. For example, the storage device 160 may be configured with a Hard Disk Drive (HDD), a Digital Versatile Disc (DVD) drive, or the like.

The input device 170 is configured to receive various types of operations performed on the X-ray CT apparatus 100 from the operator. For example, the input device 170 may be configured with a keyboard, a mouse, and/or the like. The display device 180 is configured to output various types of images generated by the reconstructing device 140 or the image processing device 150 and a Graphical user Interface (GUI) for receiving various types of operations from the operator. For example, the display device 180 may be configured with a liquid crystal panel, a Cathode Ray Tube (CRT) monitor, or the like.

The system controller 190 is configured to control overall operations of the X-ray CT apparatus 100 on the basis of the various types of operations received by the input device 170.

Further, the system controller 190 is configured to bundle the X-ray transmission signals detected by the detecting elements in one or more predetermined units, by controlling the bundling controlling unit 200 (explained later), on the basis of a scan condition. This process will be referred to as a "signal bundling process", and details thereof will be explained later.

The X-ray CT apparatus 100 according to the first embodiment configured as described above makes it possible to perform the signal bundling process in both the channel direction and the slice direction by performing the processes described below. In the following sections, a process performed by the bundling controlling unit 200 included in the X-ray CT apparatus 100 in order to realize this function will be explained.

Under the control of the system controller 190, the bundling controlling unit 200 performs the signal bundling process. In this situation, the signal bundling process is to combine together analog signals detected by the plurality of detecting elements, in one or more predetermined units, in at least one direction selected from the channel direction and the slice direction. By changing the combining units (a combining mode), it is possible to adjust the resolution of the X-ray transmission signals forwarded to the DASs. For example, in the example illustrated in FIG. 3, the combining modes changeable by the bundling controlling unit 200 are realized in the following three patterns: four detecting elements are combined into one unit (a four-element combining mode); two detecting elements are combined into one unit (a two-element combining mode); and no detecting elements are combined (a non-combining mode).

Figure 4A:
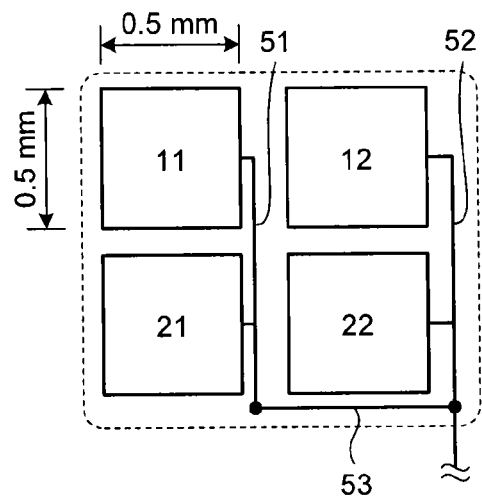
FIG. 4A to 4C are drawings for explaining a combining mode.
Figure 4B:
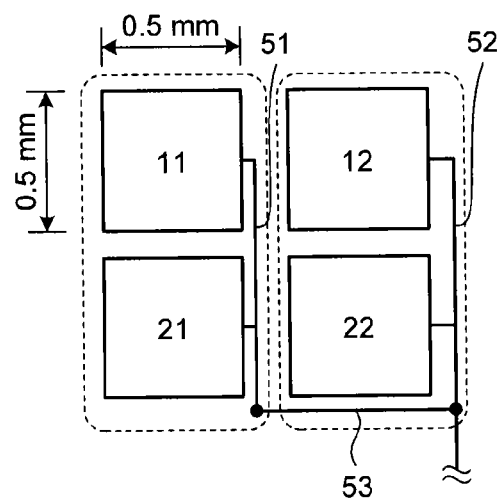
Figure 4C:
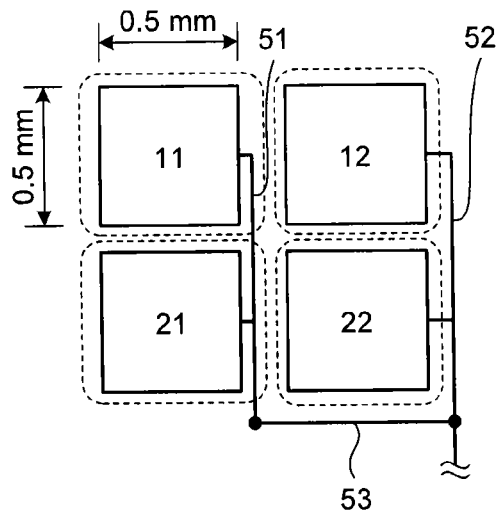

The combining modes that are changeable by performing the signal bundling process will be explained, with reference to FIG. 4A to 4C. FIG. 4A to 4C illustrate the four detecting elements 11, 12, 21, and 22 assigned to the DAS 116A illustrated in FIG. 3. FIG. 4A is a drawing for explaining the four-element combining mode. FIG. 4B is a drawing for explaining the two-element combining mode. FIG. 4C is a drawing for explaining the non-combining mode. In the examples illustrated in FIG. 4A to 4C, the lengths in the channel direction and the slice direction of each detecting elements 11, 12, 21, and 22 are 0.5-mm.

The four-element combining mode

The four-element combining mode will be explained, with reference to FIG. 4A. In this situation, for example, the bundling controlling unit 200 combines the signals (the electric charges) detected by the detecting elements 11, 12, 21, and 22, by individually controlling the switches between the DAS 116A and the four detecting elements 11, 12, 21, and 22.

More specifically, the bundling controlling unit 200 first switches on the connection between the DAS 116A and the detecting element 11. As a result, the electric charge stored in the detecting element 11 moves to a capacitor in the DAS 116A. Next, the bundling controlling unit 200 switches on the connection between the DAS 116A and the detecting element 21. As a result, the electric charge stored in the detecting element 21 moves to the capacitor in the DAS 116A and is added to the electric charge that is already stored therein. Subsequently, the bundling controlling unit 200 switches on the connection between the DAS 116A and the detecting element 12. As a result, the electric charge stored in the detecting element 12 moves to the capacitor in the DAS 116A and is further added to the electric charges that are already stored therein. After that, the bundling controlling unit 200 switches on the connection between the DAS 116A and the detecting element 22. As a result, the electric charge stored in the detecting element 22 moves to the capacitor in the DAS 116A and is further added to the electric charges that are already stored therein. In other words, the electric charges each of which was stored in a different one of the four detecting elements 11, 12, 21, and 22 are added together (combined) in the DAS 116A.

After that, the bundling controlling unit 200 causes the DAS 116A to perform a signal processing process. In other words, the DAS 116A converts the combined signals to data of digital signals (raw data). After that, the bundling controlling unit 200 resets the electric charges stored in the capacitor in the DAS 116A.

As explained above, the bundling controlling unit 200 combines the signals detected by the four detecting elements 11, 12, 21, and 22. After that, the bundling controlling unit 200 causes the combined signals to be converted into the raw data and causes the raw data to be output. In the four-element combining mode using the detecting elements each having a width of 0.5 mm, the reconstructed image data has a spatial resolution that is equivalent to the spatial resolution obtained by detecting elements each having a width of 1 mm.

The Two-Element Combining Mode

The two-element combining mode will be explained, with reference to FIG. 4B. In this situation, for example, the bundling controlling unit 200 combines the signals for sets each made up of two detecting elements, by individually controlling the switches between the DAS 116A and the four detecting elements 11, 12, 21, and 22. In the present example, as indicated with dotted lines in FIG. 4B, an example will be explained in which the signals are combined for a set made up of the detecting elements 11 and 21 and another set made up of the detecting elements 12 and 22.

More specifically, the bundling controlling unit 200 first switches on the connection between the DAS 116A and the detecting element 11. As a result, the electric charge stored in the detecting element 11 moves to a capacitor in the DAS 116A. Next, the bundling controlling unit 200 switches on the connection between the DAS 116A and the detecting element 21. As a result, the electric charge stored in the detecting element 21 moves to the capacitor in the DAS 116A and is added to the electric charge that is already stored therein. Subsequently, the bundling controlling unit 200 causes the DAS 116A to perform a signal processing process. In other words, the DAS 116A combines together the signals detected by the two detecting elements 11 and 21 and further converts the combined signals into raw data. After that, the bundling controlling unit 200 resets the electric charges stored in the capacitor in the DAS 116A.

Subsequently, the bundling controlling unit 200 switches on the connection between the DAS 116A and the detecting element 12. As a result, the electric charge stored in the detecting element 12 moves to the capacitor in the DAS 116A. After that, the bundling controlling unit 200 switches on the connection between the DAS 116A and the detecting element 22. As a result, the electric charge stored in the detecting element 22 moves to the capacitor in the DAS 116A and is added to the electric charge that is already stored therein. Subsequently, the bundling controlling unit 200 causes the DAS 116A to perform a signal processing process. In other words, the DAS 116A combines together the signals detected by the two detecting elements 12 and 22 and further converts the combined signals into raw data. After that, the bundling controlling unit 200 resets the electric charges stored in the capacitor in the DAS 116A.

As explained above, the bundling controlling unit 200 causes the raw data derived from the two detecting elements 11 and 21 and the raw data derived from the two detecting elements 12 and 22 to be sequentially output, by combining the signals for the sets each made up of two detecting elements. In the two-element combining mode using the detecting elements each having a width of 0.5 mm, the reconstructed image data has a spatial resolution in the channel direction that is twice as high as the spatial resolution obtained by detecting elements each having a width of 1 mm.

With reference to FIG. 4B, the example was explained in which the signals are combined for the set made up of the detecting elements 11 and 21 and for the set made up of the detecting elements 12 and 22. However, possible embodiments are not limited to this example. For instance, it is possible to combine signals for any arbitrary sets of detecting elements, by changing, as necessary, the order in which the connections (the switches) of the detecting elements to the DAS 116A are switched on.

The Non-Combining Mode

Next, the non-combining mode will be explained, with reference to FIG. 4C. In this situation, for example, the bundling controlling unit 200 causes the signals from the detecting elements to be output without being combined, by individually controlling the switches between the DAS 116A and the four detecting elements 11, 12, 21, and 22.

More specifically, the bundling controlling unit 200 first switches on the connection between the DAS 116A and the detecting element 11. As a result, the electric charge stored in the detecting element 11 moves to a capacitor in the DAS 116A. After that, the bundling controlling unit 200 causes the DAS 116A to perform a signal processing process. In other words, the DAS 116A converts the signal detected by the detecting element 11 into raw data. After that, the bundling controlling unit 200 resets the electric charge stored in the capacitor in the DAS 116A.

Subsequently, the bundling controlling unit 200 switches on the connection between the DAS 116A and the detecting element 21. As a result, the electric charge stored in the detecting element 21 moves to the capacitor in the DAS 116A. After that, the bundling controlling unit 200 causes the DAS 116A to perform a signal processing process. In other words, the DAS 116A converts the signal detected by the detecting element 21 into raw data. After that, the bundling controlling unit 200 resets the electric charge stored in the capacitor in the DAS 116A.

Subsequently, in a similar manner, the bundling controlling unit 200 sequentially switches on the connections between the DAS 116A and each of the detecting elements 21 and 22. After that, the bundling controlling unit 200 causes a signal processing process to be performed on each of the stored electric charges.

As explained above, the bundling controlling unit 200 sequentially causes the pieces of raw data to be output without combining the signals from the detecting elements 11, 21, 12, and 22, the pieces of raw data namely being the raw data derived from the signal from the detecting element 11, the raw data derived from the signal from the detecting element 21, the raw data derived from the signal from the detecting element 12, and the raw data derived from the signal from the detecting element 22. In the non-combining mode using the detecting elements each having a width of 0.5 mm, the reconstructed image data has a spatial resolution four times higher (two times in the channel direction and two times in the slice direction) than the spatial resolution obtained by detecting elements each having a width of 1 mm.

With reference to FIG. 4C, the example was explained in which the pieces of raw data are sequentially output by turning on the switches for the detecting elements 11, 21, 12, and 22, in the stated order. However, possible embodiments are not limited to this example. For instance, it is possible to output the pieces of raw data in any arbitrary order, by changing, as necessary, the order in which the connections (the switches) of the detecting elements to the DAS 116A are switched on.

As explained above, by performing the signal bundling process, the bundling controlling unit 200 changes the quantity of effective detecting elements in the channel direction and the slice direction. The signal bundling process has an advantageous effect where noise levels of the individual detecting elements are averaged. In other words, by combining the signals from the plurality of detecting elements together, it is possible to obtain a piece of raw data that is equivalent to a piece of raw data obtained from detecting elements having a larger size. As a result, although the spatial resolution becomes lower, resistance to noise is enhanced.

In other words, in order to achieve a desired level of spatial resolution or in order to achieve a desired S/N ratio, the bundling controlling unit 200 performs an image taking process by switching between the combining modes described above. As a result, the bundling controlling unit 200 is able to address both of the situations where images are taken with a high spatial resolution and where images are taken with a high S/N ratio.

Figure 5:
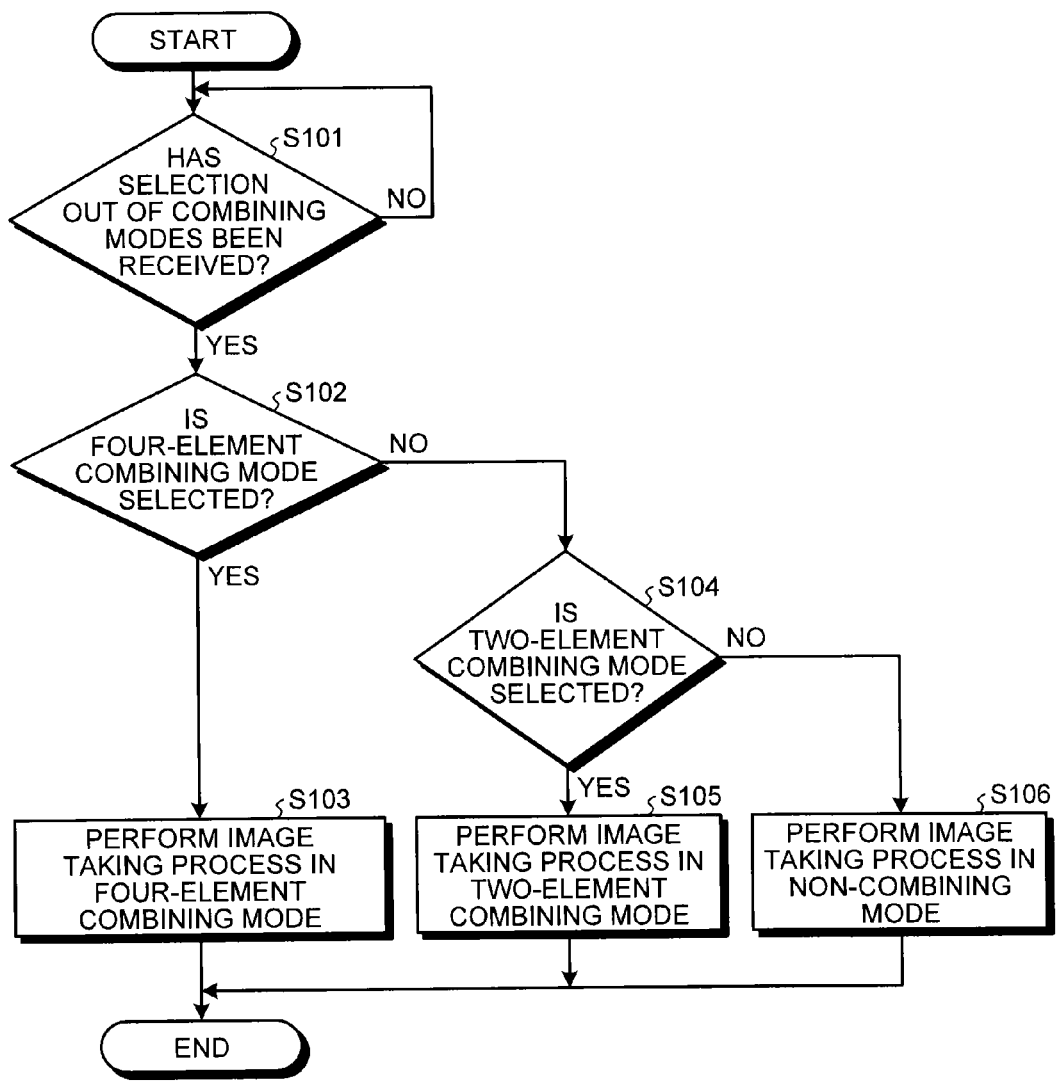
FIG. 5 is a flowchart of a processing procedure in a combining mode switching process according to the first embodiment.

FIG. 5 is a flowchart of a processing procedure in a combining mode switching process according to the first embodiment. As illustrated in FIG. 5, the bundling controlling unit 200 receives a selection out of the combining modes (step S101). For example, the bundling controlling unit 200 causes the selectable combining modes to be displayed with a Graphical User Interface (GUI) and receives a selection out of the combining modes from the operator. In a specific example, the bundling controlling unit 200 receives a selection out of the four-element combining mode, the two-element combining mode, and the non-combining mode. In this situation, the bundling controlling unit 200 is in a stand-by state, until a selection out of the combining modes is received (step S101: No).

When having received a selection out of the combining modes (step S101: Yes), the bundling controlling unit 200 judges whether the selected combining mode is the four-element combining mode (step S102). If the selected combining mode is the four-element combining mode (step S102: Yes), the bundling controlling unit 200 causes an image taking process to be performed in the four-element combining mode (step S103).

In contrast, if the selected combining mode is not the four-element combining mode (step S102: No), the bundling controlling unit 200 judges whether the selected combining mode is the two-element combining mode (step S104). If the selected combining mode is the two-element combining mode (step S104: Yes), the bundling controlling unit 200 causes an image taking process to be performed in the two-element combining mode (step S105).

In contrast, if the selected combining mode is not the two-element combining mode (step S104: No), the bundling controlling unit 200 causes an image taking process to be performed in the non-combining mode (step S106).

The processing procedure in the combining mode switching process is not limited to the example described above. For example, the bundling controlling unit 200 may obtain, from the system controller 190, a group of image taking conditions (protocols) set in advance at an image taking planning stage. Further, because the group of image taking conditions has incorporated therein, in advance, appropriate combining modes corresponding to the different image taking conditions, the bundling controlling unit 200 may switch between the combining modes by referring to the appropriate combining modes.

As explained above, in the X-ray CT apparatus 100 according to the first embodiment, the X-ray tube 111 is configured to generate the X-rays by rotating around the body axis of the subject. Further, in the X-ray CT apparatus 100, within the X-ray detector 115, the plurality of detecting elements each of which is configured to detect the X-rays that have passed through the subject are arranged in the body-axis direction of the subject and in the rotation direction in which the X-ray tube 111 rotates. Each of the DASs is configured to acquire the signals of the X-rays detected by at least one group of detecting elements including the predetermined quantity of detecting elements. In the group of detecting elements, a plurality of detecting elements are arranged in at least the rotation direction. With these arrangements, the X-ray CT apparatus 100 according to the first embodiment makes it possible to perform the signal bundling process in both the channel direction and the slice direction.

Further, for example, the X-ray CT apparatus 100 according to the first embodiment performs the image taking process by switching between the predetermined combining modes, in order to achieve a desired level of spatial resolution or in order to achieve a desired S/N ratio. As a result, the X-ray CT apparatus 100 is able to address both of the situations where images are taken with a high spatial resolution and where images are taken with a high S/N ratio.

In other words, the X-ray CT apparatus 100 according to the first embodiment includes the X-ray tube 111, the X-ray detector 115, the DASs 116A to 116D serving as an acquiring unit, and the reconstructing device 140 serving as an image generating unit. The X-ray tube 111 is configured to generate the X-rays by rotating around the body axis of the subject. In the X-ray detector 115, the plurality of detecting elements each of which is configured to detect the X-rays that have passed through the subject are arranged in the body-axis direction of the subject and in the rotation direction in which the X-ray tube rotates. Each of the DASs 116A to 116D is configured to acquire the signals of the X-rays detected by at least one group of detecting elements which includes the predetermined quantity of detecting elements and in which a plurality of detecting elements are arranged in at least the rotation direction. The reconstructing device 140 is configured to generate the image by using the signals acquired by the acquiring unit.

A modification example of the first embodiment

Figure 6:
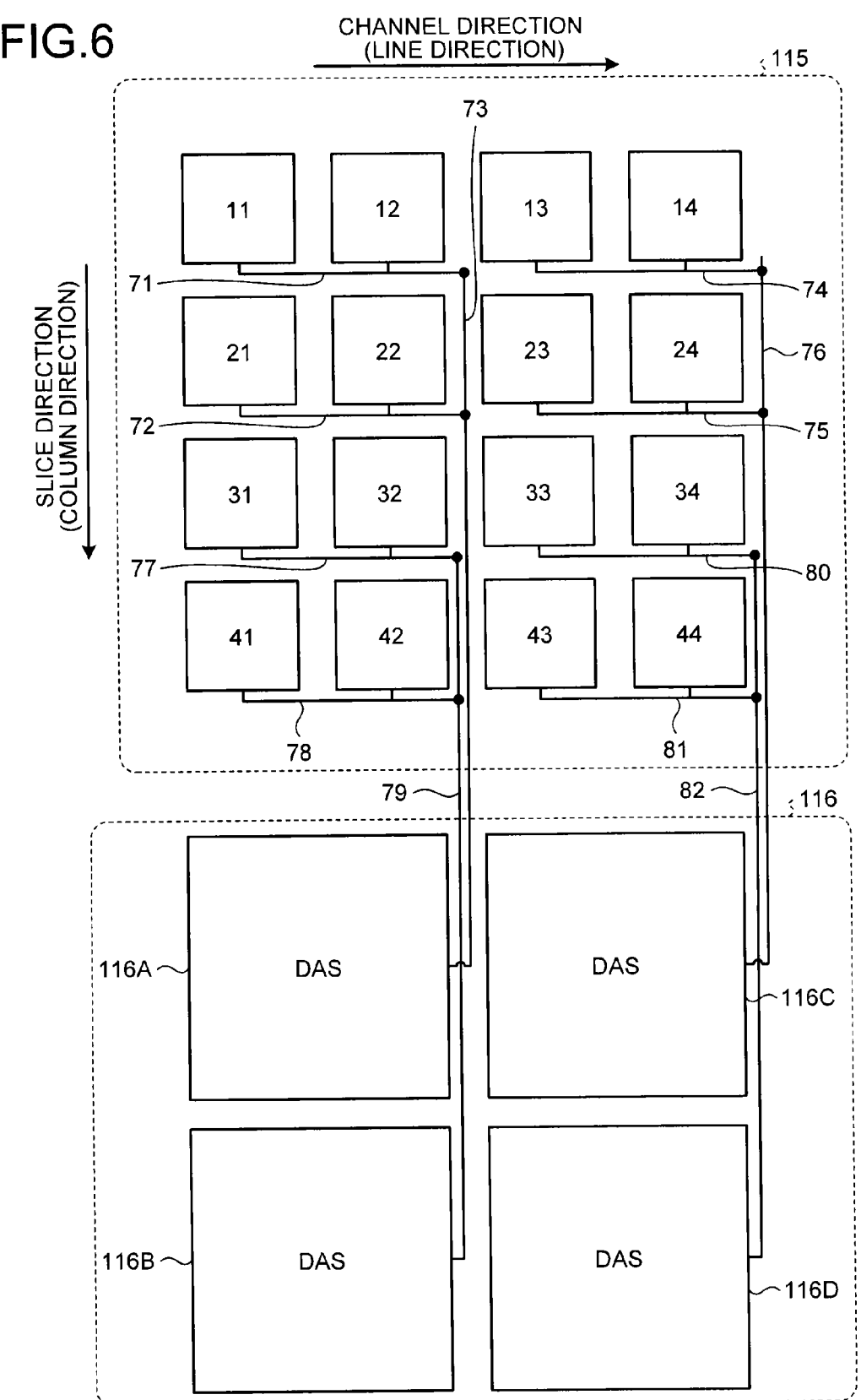
FIG. 6 is a drawing for explaining a modification example of a positional relationship between the DASs and the detecting elements according to the first embodiment.

The positional relationship between the DASs and the detecting elements explained with reference to FIG. 3 is merely an example. For instance, the positional relationship may be modified as illustrated in FIG. 6. FIG. 6 is a drawing for explaining a modification example of the positional relationship between the DASs and the detecting elements in the first embodiment. Although the alignment of the detecting elements and the DASs illustrated in FIG. 6 is the same as the alignment illustrated in FIG. 3, the positional arrangements of the lead wires connected to the detecting elements are different.

In FIG. 6, the DAS 116A is in charge of processing the signals detected by the detecting elements 11, 12, 21, and 22. In this situation, the detecting elements 11 and 12 are present in mutually-different positions in the channel direction. Also, the detecting elements 21 and 22 are present in mutually-different positions in the channel direction. Further, the detecting elements 11 and 21 are present in mutually-different positions in the slice direction. Also, the detecting elements 12 and 22 are present in mutually-different positions in the slice direction. Further, a lead wire 71 is configured to connect the detecting elements 11 and 12 together that are provided in the same slice. Further, a lead wire 72 is configured to connect the detecting elements 21 and 22 together that are provided in the same slice. Furthermore, a lead wire 73 is configured to connect the lead wires 71 and 72 together. In addition, the lead wires 71, 72, and 73 are connected to the DAS 116A. In the example illustrated in FIG. 6, the lead wire 73 is connected to the DAS 116A. Provided between the detecting elements 11, 12, 21, 22 and the DAS 116A are switches configured to individually switch the connection and the disconnection between the detecting elements and the DAS. Further, in the present description, for the sake of convenience in the explanation, the example in which the lead wires 71, 72, and 73 are each connected is explained. However, possible embodiments are not limited to this example. For instance, the lead wires 71, 72, and 73 may be configured with a single lead wire.

Further, the DAS 116B is in charge of processing the signals detected by the detecting elements 31, 32, 41, and 42. In this situation, the positional relationship among the DAS 116B, the detecting elements 31, 32, 41, and 42, lead wires 77, 78, and 79 is the same as the positional relationship among the DAS 116A, the detecting elements 11, 12, 21, and 22, and the lead wires 71, 72, and 73.

Further, the DAS 116C is in charge of processing the signals detected by the detecting elements 13, 14, 23, and 24. In this situation, the positional relationship among the DAS 116C, the detecting elements 13, 14, 23, and 24, lead wires 74, 75, and 76 is the same as the positional relationship among the DAS 116A, the detecting elements 11, 12, 21, and 22, and the lead wires 71, 72, and 73.

Furthermore, the DAS 116D is in charge of processing the signals detected by the detecting elements 33, 34, 43, and 44. In this situation, the positional relationship among the DAS 116D, the detecting elements 33, 34, 43, and 44, lead wires 80, 81, and 82 is the same as the positional relationship among the DAS 116A, the detecting elements 11, 12, 21, and 22, and the lead wires 71, 72, and 73.

As explained above, the DASs 116A to 116D read data from the detecting elements 11 to 44. The DASs 116A to 116D are capable of performing the reading processes in parallel to one another.

Second Embodiment

In the first embodiment, the example is explained in which each of the DASs is in charge of processing the signals detected by the plurality of detecting elements in the channel direction and the slice direction. In that situation, when one DAS reads signals from a plurality of detecting elements, strictly speaking, X-ray emission periods (time periods) vary among the detecting elements.

Figure 7:
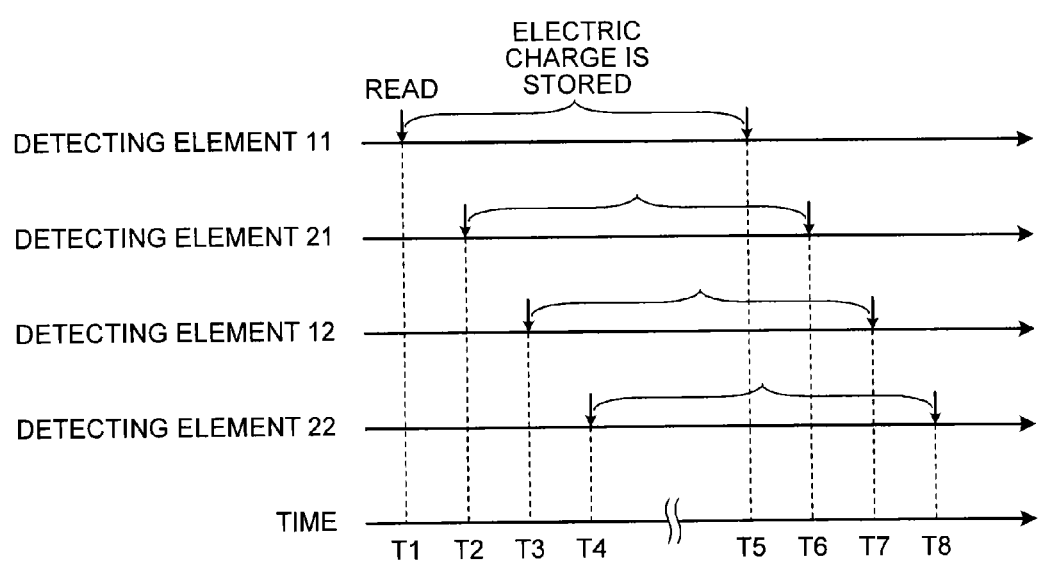
FIG. 7 is a drawing for explaining a relationship between reading of signals from the detecting elements and emission periods.

FIG. 7 is a drawing for explaining a relationship between reading of signals from the detecting elements and the emission periods. In FIG. 7, the horizontal direction corresponds to time. The arrows pointing downwards indicate times at which the signals (the electric charges) are read. FIG. 7 illustrates an example with the detecting elements 11, 21, 12, and 22. However, the same applies to the other detecting elements included in the X-ray detector 115.

As illustrated in FIG. 7, when reading signals from the detecting elements 11, 21, 12, and 22, the DAS 116A reads the signals (the electric charges) at mutually-different times, i.e., T1 to T8. In this situation, for example, the signal read at the time T5 corresponds to the emission from the time T1 to the time T5. The signal read at the time T6 corresponds to the emission from the time T2 to the time T6. The signal read at the time T7 corresponds to the emission from the time T3 to the time T7. The signal read at the time T8 corresponds to the emission from the time T4 to the time T8.

As explained above, strictly speaking, the signals read by the DAS 116A may correspond to the emissions in mutually-different time periods. For this reason, it is desirable to correct the raw data output from each of the detecting elements, by using an X-ray amount corresponding to the time at which X-rays were emitted onto the detecting element. Thus, in a second embodiment, an example will be explained in which the X-ray CT apparatus 100 corrects the raw data output from each of the detecting elements, by using an X-ray amount corresponding to the time at which X-rays were emitted onto the detecting element of which a corresponding one of the DASs is in charge.

Figure 8:
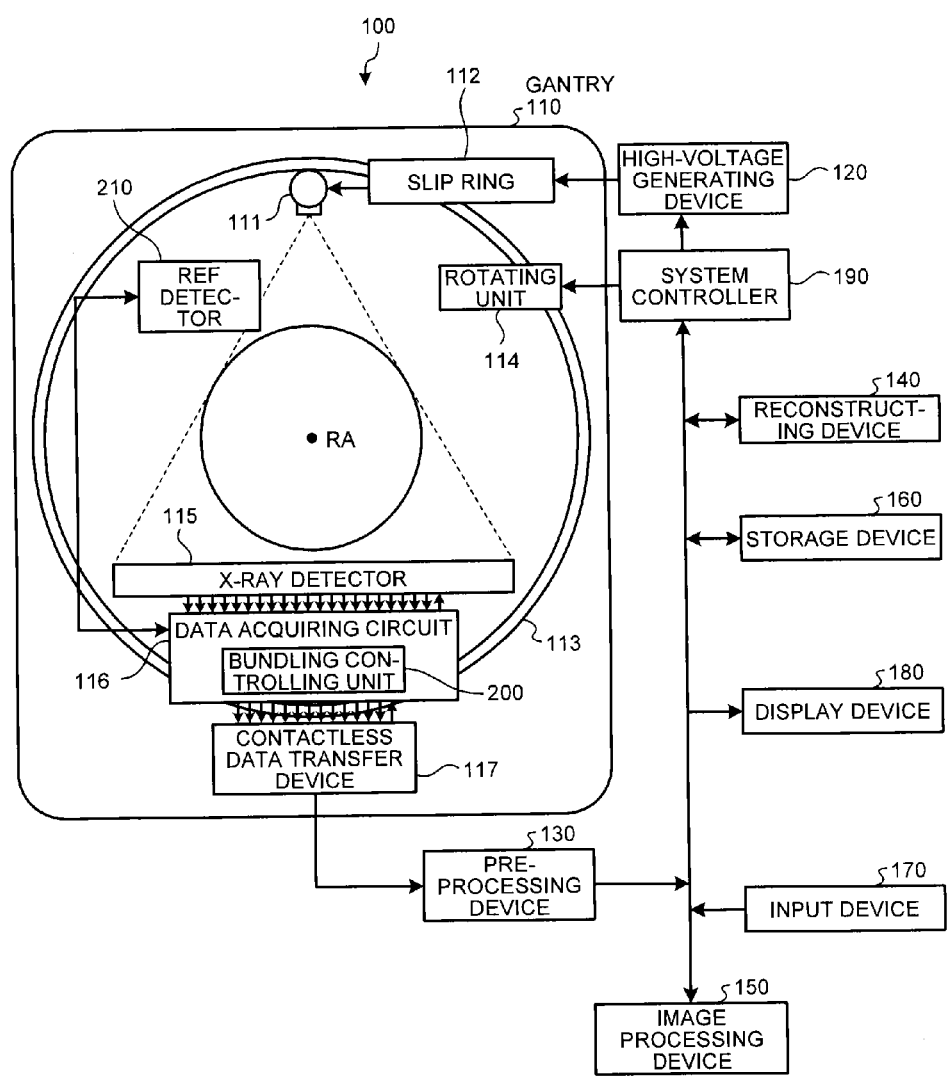
FIG. 8 is a drawing for explaining a configuration of an X-ray CT apparatus according to a second embodiment.

FIG. 8 is a drawing of a configuration of the X-ray CT apparatus 100 according to the second embodiment. The X-ray CT apparatus 100 according to the second embodiment has a configuration similar to the configuration of the X-ray CT apparatus 100 illustrated in FIG. 1 and is different because of having a reference (Ref) detector 210 provided near the X-ray tube 111 and because of a part of the processes performed by the data acquiring circuit 116 and the pre-processing device 130. Thus, the second embodiment will be explained while a focus is placed on the differences from the first embodiment. The explanation of the features having the same functions as those explained in the first embodiment will be omitted.

The Ref detector 210 according to the second embodiment includes a detecting element. The detecting element included in the Ref detector 210 is configured to detect signals of the X-rays that do not pass through the subject (hereinafter, "X-ray non-transmission signals"). After that, the detecting element included in the Ref detector 210 sequentially outputs the detected X-ray non-transmission signals to the data acquiring circuit 116. It is desirable to configure the detecting element by using the same materials as those of the detecting elements 11 to 44.

The data acquiring circuit 116 according to the second embodiment has the functions that are the same as those explained in the first embodiment. Further, the data acquiring circuit 116 includes a DAS (Ref-purpose DAS) configured to process the X-ray non-transmission signals detected by the Ref detector 210.

The Ref-purpose DAS is configured to generate data (reference data) corresponding to the emission periods of the detecting elements in the X-ray detector 115, on the basis of the X-ray non-transmission signals detected by the Ref detector 210. In other words, the Ref-purpose DAS acquires correction signals used in a correcting process performed when an image is generated. The Ref-purpose DAS individually acquires the correction signals corresponding to the times at which the signals acquired by the DASs 116A to 116D are read.

Figure 9C:
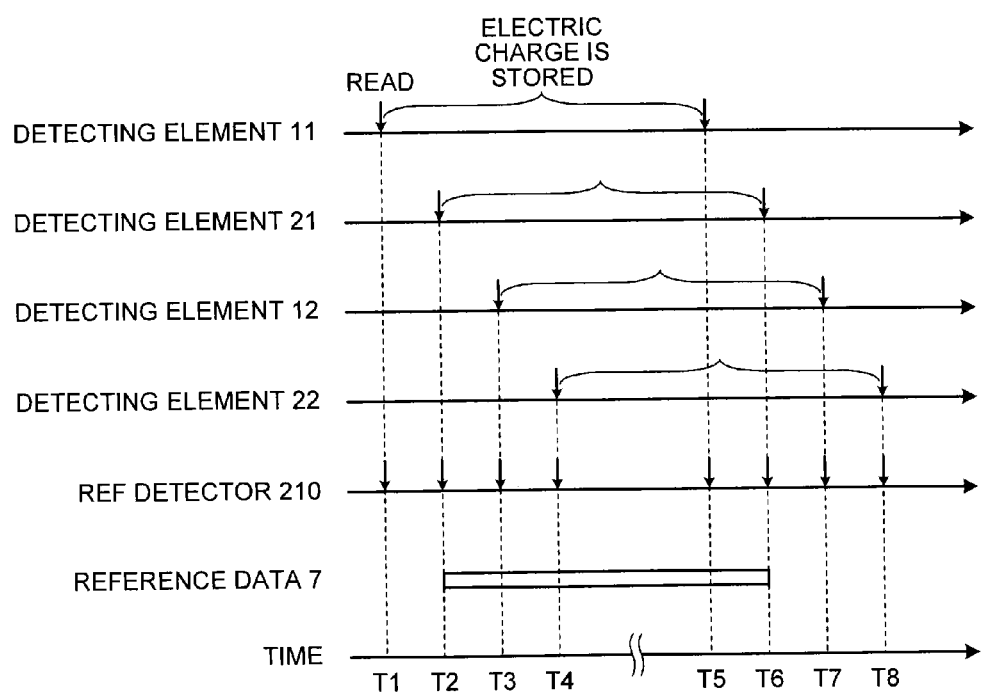

FIG. 9A to 9C are drawings for explaining the generation of the reference data according to the second embodiment. In FIG. 9A to 9C, the horizontal direction corresponds to time. The example illustrated in FIG. 9A explains reference data generated in the non-combining mode. The example illustrated in FIG. 9B explains reference data generated in the two-element combining mode. The example illustrated in FIG. 9C explains reference data generated in the four-element combining mode.

As illustrated in FIG. 9A, in the non-combining mode, the Ref-purpose DAS generates reference data 1, 2, 3, and 4 for pieces of raw data output from the detecting elements, respectively.

More specifically, the Ref-purpose DAS includes a capacitor and stores therein the X-ray non-transmission signals (the electric charges) output from the Ref detector 210. After that, the Ref-purpose DAS reads the signals stored in the capacitor at the times at which the signals are read from the detecting elements 11, 12, 21, and 22. In the example illustrated in FIG. 9A, the Ref-purpose DAS reads the signals at the times T1, T2, . . . , and T8. The signals read in this situation correspond to the electric charges stored according to the non-transmission X-rays during the time periods of T1 to T2, T2 to T3, . . . , and T7 to T8. After that, the Ref-purpose DAS amplifies the signals read for the mutually-different time periods and further converts the amplified signals into data (period data) of digital signals. The period data corresponds to a moving average of the signals for each of the time periods. In other words, the Ref-purpose DAS individually acquires the correction signals corresponding to the times at which the signals acquired by the DASs 116A to 116D are read, by obtaining the moving average of the signals of the X-rays detected without having passed through the subject.

After that, as illustrated in FIG. 9A, the Ref-purpose DAS generates reference data corresponding to the time periods during which X-rays were emitted onto the detecting elements 11, 12, 21, and 22. More specifically, the Ref-purpose DAS generates a piece of reference data corresponding to each of the detecting elements, by adding pieces of period data together. For example, for the detecting element 11, the Ref-purpose DAS generates the reference data 1 by adding together pieces of period data corresponding to the interval (T1 to T5) between the reading times of the detecting element 11. As another example, for the detecting element 21, the Ref-purpose DAS generates the reference data 2 by adding together pieces of period data corresponding to the interval (T2 to T6) between the reading times of the detecting element 21. As yet another example, for the detecting element 12, the Ref-purpose DAS generates the reference data 3 by adding together pieces of period data corresponding to the interval (T3 to T7) between the reading times of the detecting element 12. As yet another example, for the detecting element 22, the Ref-purpose DAS generates the reference data 4 by adding together pieces of period data corresponding to the interval (T4 to T8) between the reading times of the detecting element 22.

After that, to each of the pieces of raw data derived from the detecting elements 11, 12, 21, and 22, the data acquiring circuit 116 appends a piece of reference data that corresponding thereto. For example, the data acquiring circuit 116 appends the reference data 1 to the raw data derived from the detecting element 11. As another example, the data acquiring circuit 116 appends the reference data 2 to the raw data derived from the detecting element 21. As yet another example, the data acquiring circuit 116 appends the reference data 3 to the raw data derived from the detecting element 12. As yet another example, the data acquiring circuit 116 appends the reference data 4 to the raw data derived from the detecting element 22.

As illustrated in FIG. 9B, in the two-element combining mode, the Ref-purpose DAS generates a piece of reference data for each of the sets made up of the detecting elements 11, 12, 21, and 22 used in the two-element combining mode, under the control of the bundling controlling unit 200. For example, the Ref-purpose DAS generates a piece of reference data corresponding to the emission period of one of the detecting elements included in each of the sets.

For example, to correct the raw data derived from the set made up of the detecting elements 11 and 21, the Ref-purpose DAS generates reference data 5 corresponding to the emission period (T1 to T5) of the detecting element 11. Because the process for generating the reference data 5 is the same as the process for generating the reference data 1 illustrated in FIG. 9A, the explanation thereof will be omitted.

As another example, to correct the raw data derived from the set made up of the detecting elements 12 and 22, the Ref-purpose DAS generates reference data 6 corresponding to the emission period (T3 to T7) of the detecting element 12. Because the process for generating the reference data 6 is the same as the process for generating the reference data 3 illustrated in FIG. 9A, the explanation thereof will be omitted.

After that, the data acquiring circuit 116 appends the reference data 5 to the raw data derived from the two detecting elements 11 and 21. Further, the data acquiring circuit 116 appends the reference data 6 to the raw data derived from the two detecting elements 12 and 22. In the example illustrated in FIG. 9B, the reference data 5 corresponding to the emission period (T1 to T5) of the detecting element 11 is generated for the purpose of correcting the raw data derived from the set made up of the detecting elements 11 and 21. However, possible embodiments are not limited to this example. For instance, it is acceptable to generate a piece of reference data (corresponding to the reference data 2 in FIG. 9A) that corresponds to the emission period (T2 to T6) of the detecting element 21. In other words, to generate the reference data in the two-element combining mode, it is sufficient if a piece of reference data corresponding to the emission period of either one of the detecting elements included in each set is generated. In other words, when the signals detected by the plurality of detecting elements included in a group of detecting elements are combined together in one or more predetermined units, the Ref-purpose DAS acquires the correction signal corresponding to the time at which one of the signals to be combined is read.

As illustrated in FIG. 9C, in the four-element combining mode, the Ref-purpose DAS generates reference data corresponding to the emission period of one of the detecting elements 11, 12, 21, and 22 used in the four-element combining mode, under the control of the bundling controlling unit 200.

For example, the Ref-purpose DAS generates reference data 7 corresponding to the emission period (T2 to T6) of the detecting element 21. Because the process for generating the reference data 7 is the same as the process for generating the reference data 2 illustrated in FIG. 9A, the explanation thereof will be omitted.

After that, the data acquiring circuit 116 appends the reference data 7 to the raw data derived from the four detecting elements 11, 12, 21 and 22. In the example illustrated in FIG. 9C, the reference data 7 corresponding to the emission period (T2 to T6) of the detecting element 21 is generated for the purpose of correcting the raw data derived from the four detecting elements 11, 12, 21, and 22. However, possible embodiments are not limited to this example. For instance, it is acceptable to generate a piece of reference data (corresponding to the reference data 3 in FIG. 9A) that corresponds to the emission period (T3 to T7) of the detecting element 12. In other words, to generate the reference data in the four-element combining mode also, it is sufficient if a piece of reference data corresponding to the emission period of any one of the detecting elements to be combined is generated. It should be noted that, however, it is desirable to generate a piece of reference data corresponding to, among the detecting elements to be combined, such a detecting element of which the emission period is near the center, for the purpose of avoiding the situation where there is a large difference between the emission period targeted by the reference data and the emission periods of the detecting elements. In other words, when the signals detected by the plurality of detecting elements included in a group of detecting elements are combined together in one or more predetermined units, the Ref-purpose DAS acquires the correction signal corresponding to a reading time near the center among reading times of the signals to be combined. Alternatively, another arrangement is acceptable in which, similarly to FIG. 9A, four pieces of reference data corresponding to the detecting elements are generated, so that an appropriate piece is selected, as necessary, from among the generated pieces of reference data.

The pre-processing device 130 according to the second embodiment is configured to perform a correcting process of correcting the pieces of raw data, by using the reference data appended to each of the pieces of raw data. For example, the pre-processing device 130 calculates an output ratio (=raw data/reference data). The output ratio expresses an attenuation of the X-rays caused by the subject.

For example, in the non-combining mode, the data acquiring circuit 116 divides the raw data derived from the detecting element 11 by the reference data 1. Further, the data acquiring circuit 116 divides the raw data derived from the detecting element 21 by the reference data 2. Also, the data acquiring circuit 116 divides the raw data derived from the detecting element 12 by the reference data 3. Furthermore, the data acquiring circuit 116 divides the raw data derived from the detecting element 22 by the reference data 4.

As another example, in the two-element combining mode, the data acquiring circuit 116 divides the raw data derived from the detecting elements 11 and 21 by the reference data 5. Furthermore, the data acquiring circuit 116 divides the raw data derived from the detecting elements 12 and 22 by the reference data 6.

As yet another example, in the four-element combining mode, the data acquiring circuit 116 divides the raw data derived from the detecting elements 11, 12, 21, and 22 by the reference data 7.

As explained above, the X-ray CT apparatus 100 according to the second embodiment makes it possible to correct the raw data output from the detecting elements in any of the combining modes, by using the X-ray amount corresponding to the time when the X-rays were emitted onto the detecting elements of which each of the DASs is in charge.

In other words, in the X-ray CT apparatus 100 according to the second embodiment, when reading the signals detected by the plurality of detecting elements arranged in the rotation direction from the X-ray detector 115, each of the DASs 116A to 116D sequentially reads the signals at the times that vary among the detecting elements arranged in the rotation direction. The Ref-purpose DAS individually acquires the correction signals corresponding to the times at which the signals acquired by the DASs 116A to 116D are read. The reconstructing device 140 generates the image by applying each of the correction signals to a corresponding one of the signals that were sequentially read at the reading times.

Other Embodiments

In the first and the second embodiments described above, the example was explained in which four detecting elements are assigned to each of the DASs. However, possible embodiments are not limited to this example. For instance, the quantity of detecting elements assigned to each of the DASs may be eight or may be two. When the quantity of detecting elements assigned to each of the DASs is two, by arranging the two detecting elements in the channel direction, it is possible to perform a signal bundling process in at least the channel direction. In other words, the group of detecting elements assigned to each of the DASs is sufficient if a plurality of detecting elements are arranged in at least the channel direction.

Figure 10:
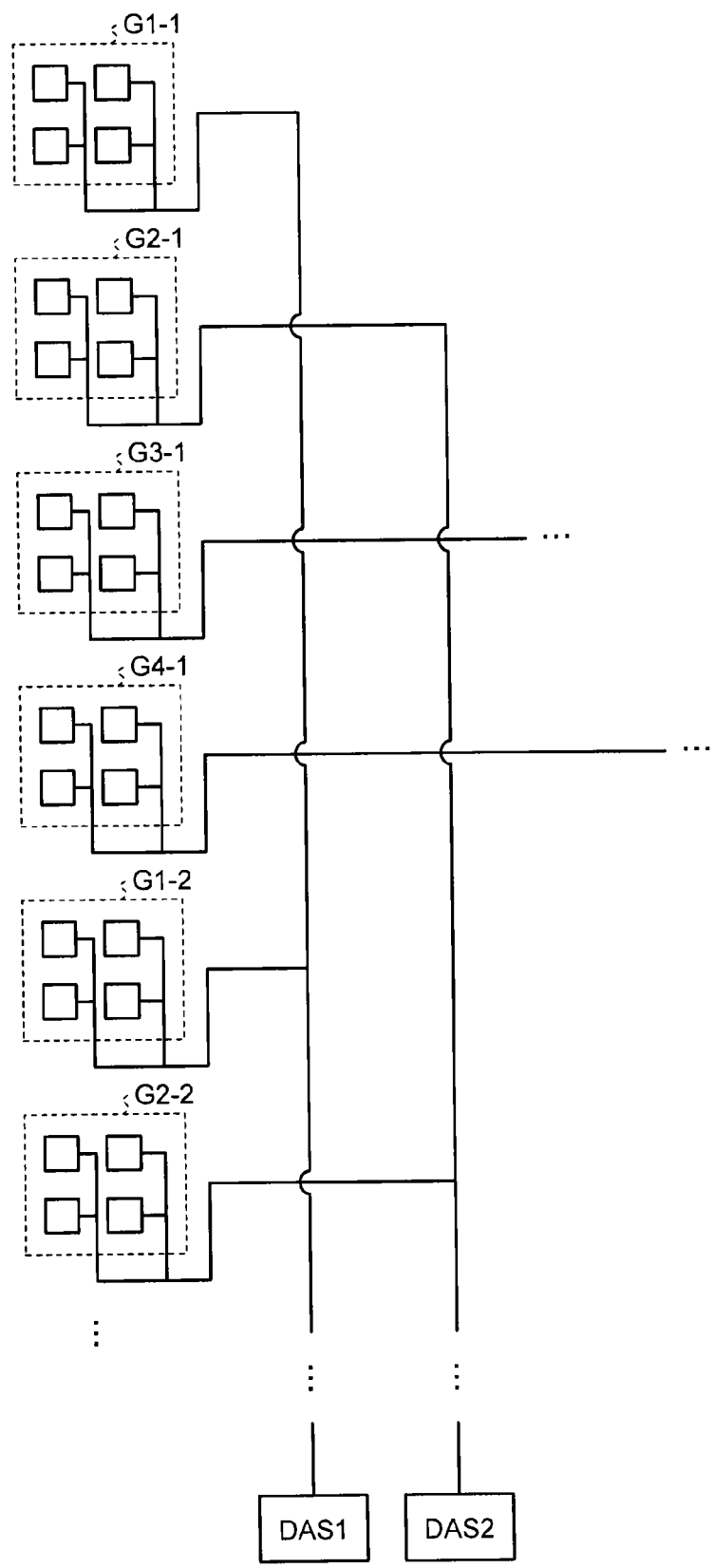
FIG. 10 is a drawing for explaining a positional relationship between DASs and detecting elements according to another embodiment.

FIG. 10 is a drawing for explaining a positional relationship between the DASs and the detecting elements according to another embodiment. FIG. 10 illustrates an example in which eight or more groups of detecting elements are assigned to each DAS. In other words, in FIG. 10, each of the groups of detecting elements G1-1, G2-1, G3-1, G4-1, G1-2, and G2-2 corresponds to a group of detecting elements made up of four detecting elements described in the exemplary embodiments above. Each of the groups is a set that is made up of a plurality of detecting elements and in which two detecting elements are arranged in the channel direction and the slice direction.

In the example illustrated in FIG. 10, for example, the group of detecting elements G1-1 and the group of detecting elements G1-2 are assigned to a single DAS that is a "DAS 1". Further, as illustrated in FIG. 10, the group of detecting elements G1-1 and the group of detecting elements G1-2 are not positioned adjacent to each other. Instead, other groups of detecting elements assigned to DASs (e.g., a "DAS 2", a "DAS 3" (not shown) and a "DAS 4" (not shown)) other than the "DAS 1" are positioned between the groups of detecting elements G1-1 and G1-2.

In the positional relationship illustrated in FIG. 10, for example, "DAS 1" first reads an electric charge from the group of detecting elements G1-1 and subsequently reads an electric charge from the group of detecting elements G1-2. In this situation, the time at which the "DAS 1" reads an electric charge from the group of detecting elements G1-1, the time at which the "DAS 2" reads the electric charge from the group of detecting elements G2-1 the time at which the "DAS 3" reads the electric charge from the group of detecting elements G3-1, the time at which the "DAS 4" reads the electric charge from the group of detecting elements G4-1 are substantially the same as one another. Thus, by assigning the groups of detecting elements that are physically positioned close to each other to mutually-different DASs to be in charge thereof, it is possible to arrange the times of the reading from the groups of detecting elements that are physically positioned close to each other to be substantially the same as one another. As a result, it is possible to contribute to enhancing the image quality.

In the second embodiment, the generation of the reference data was explained. The process will be further explained, with reference to FIG. 10. For example, as explained for the non-combining mode in the second embodiment, let us assume that pieces of reference data are individually generated so as to correspond to the X-ray emission periods of the detecting elements. In the example illustrated in FIG. 10, four pieces of reference data are generated for the group of detecting elements G1-1, and the same pieces of reference data are also applied to the group of detecting elements G2-1, the group of detecting elements G3-1, and the group of detecting elements G4-1. Further, four pieces of reference data are generated also for the group of detecting elements G1-2 and for the group of detecting elements G2-2, but these pieces of reference data are different from the pieces of reference data generated for the group of detecting elements G1-1 or the group of detecting elements G2-1.

As another example, as explained for the four-element combining mode in the second embodiment, let us assume that one representative piece of reference data corresponding to one of the detecting elements is applied. In that situation, in the example illustrated in FIG. 10, one piece of reference data is generated for the group of detecting elements G1-1, and the same piece of reference data is also applied to the group of detecting elements G2-1, the group of detecting elements G3-1, and the group of detecting elements G4-1. Further, one piece of reference data is also generated for the group of detecting elements G1-2 and for the group of detecting elements G2-2, but these pieces of reference data are different from the pieces of reference data generated for the group of detecting elements G1-1 or the group of detecting elements G2-1.

An application to an X-ray diagnosis apparatus

In the exemplary embodiments described above, the examples are explained in which the disclosed feature is applied to the X-ray CT apparatus. However, possible embodiments are not limited to those examples. For instance, the disclosed feature may be applied to an X-ray diagnosis apparatus.

In other words, an X-ray diagnosis apparatus includes an X-ray tube, an X-ray detector, a plurality of acquiring units, an image generating unit, and a correction signal acquiring unit. The X-ray tube is configured to generate X-rays. In the X-ray detector, a plurality of groups of detecting elements are arranged in a two-dimensional direction, the groups of detecting elements each including a predetermined quantity of detecting elements each of which is configured to detect X-rays that have passed through a subject. The plurality of acquiring units are configured to acquire signals of X-rays detected by the detecting elements. The image generating unit is configured to generate an image by using the signals acquired by the plurality of acquiring units. The correction signal acquiring unit is configured to acquire correction signals used in a correcting process performed when the image is generated by the image generating unit. Further, when reading the signals detected by the predetermined quantity of detecting elements included in each of the groups of detecting elements from the X-ray detector, each of the acquiring units sequentially reads the signals at times that vary among the predetermined quantity of detecting elements. The correction signal acquiring unit individually acquires correction signals corresponding to the times at which the signals are read. After that, the image generating unit generates the image by applying each of the correction signals to a corresponding one of the signals that were sequentially read at the signal reading times.

According to at least one aspect of the embodiments described above, it is possible to perform the signal bundling process both in the channel direction and the slice direction.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
   an X-ray tube configured to generate X-rays by rotating around a body axis of a subject;
   an X-ray detector in which a plurality of detecting elements each of which is configured to detect X-rays that have passed through the subject are arranged in a body-axis direction of the subject and in a rotation direction in which the X-ray tube rotates;
   an acquiring unit configured to acquire signals of the X-rays detected by at least one group of detecting elements which includes a predetermined quantity of detecting elements and in which a plurality of detecting elements are arranged in at least the rotation direction;
   an image generating unit configured to generate an image by using the signals acquired by the acquiring unit; and
   a correction signal acquiring unit configured to acquire correction signals used in a correcting process performed when the image is generated by the image generating unit, wherein
   when reading the signals detected by a plurality of detecting elements arranged in the rotation direction from the X-ray detector, the acquiring unit sequentially reads the signals at times that vary among the detecting elements arranged in the rotation direction,
   the correction signal acquiring unit individually acquires the correction signals corresponding to the times at which the signals are read, and
   the image generating unit generates the image by applying each of the correction signals to a corresponding one of the signals that were sequentially read at the reading times.

2. The X-ray CT apparatus according to claim 1, wherein the correction signal acquiring unit individually acquires the correction signals corresponding to the times at which the signals are read, by obtaining a moving average of signals of X-rays detected without having passed through the subject.

3. The X-ray CT apparatus according to claim 1, wherein, when the signals detected by the plurality of detecting elements included in the group of detecting elements are combined together in one or more predetermined units, the correction signal acquiring unit acquires the correction signal corresponding to a time at which one of the signals to be combined is read.

4. The X-ray CT apparatus according to claim 1, wherein, when the signals detected by the plurality of detecting elements included in the group of detecting elements are combined together in one or more predetermined units, the correction signal acquiring unit acquires the correction signal corresponding to a reading time near a center among reading times of the signals to be combined.

5. The X-ray CT apparatus according to claim 1, wherein the image generating unit generates the image in accordance with switching between a first mode in which signals detected by a plurality of detecting elements arranged in the rotation direction among the group of detecting elements are combined together and output from the acquiring unit and a second mode in which the signals detected by the plurality of detecting elements arranged in the rotation direction are each individually output from the acquiring unit.

6. The X-ray CT apparatus according to claim 1, wherein in the group of detecting elements, a plurality of detecting elements are further arranged in the body-axis direction.

7. The X-ray CT apparatus according to claim 6, further comprising:
   a plurality of first lead wires configured to connect together a plurality of detecting elements arranged in the body-axis direction; and
   a second lead wire configured to connect together the plurality of first lead fires arranged in the rotation direction.

8. The X-ray CT apparatus according to claim 7, wherein the acquiring unit combines together signals detected by the plurality of detecting elements arranged in the body-axis direction.

9. The X-ray CT apparatus according to claim 6, further comprising:
   a plurality of first lead wires configured to connect together a plurality of detecting elements arranged in the rotation direction; and
   a second lead wire configured to connect together the plurality of first lead fires arranged in the body-axis direction.

10. The X-ray CT apparatus according to claim 9, wherein the acquiring unit combines together signals detected by the plurality of detecting elements arranged in the rotation direction.

11. An X-ray diagnosis apparatus comprising:
    an X-ray tube configured to generate X-rays;
    an X-ray detector in which a plurality of groups of detecting elements are arranged in a two-dimensional direction, the groups of detecting elements each including a predetermined quantity of detecting elements each of which is configured to detect X-rays that have passed through a subject;
    a plurality of acquiring units configured to acquire signals of the X-rays detected by the detecting elements;
    an image generating unit configured to generate an image by using the signals acquired by the plurality of acquiring units; and
    a correction signal acquiring unit configured to acquire correction signals used in a correcting process performed when the image is generated by the image generating unit, wherein
    when reading the signals detected by the predetermined quantity of detecting elements included in each of the groups of detecting element from the X-ray detector, each of the acquiring units sequentially reads the signals at times that vary among the predetermined quantity of detecting elements,
    the correction signal acquiring unit individually acquires the correction signals corresponding to the times at which the signals are read, and the image generating unit generates the image by applying each of the correction signals to a corresponding one of the signals that were sequentially read at the reading times.

* * * * *